(12) United States Patent
Mizoguchi et al.

(10) Patent No.: US 9,041,406 B2
(45) Date of Patent: May 26, 2015

(54) INSULATION DETERIORATION DETECTION APPARATUS

(71) Applicant: DENSO CORPORATION, Kariya, Aichi-pref. (JP)

(72) Inventors: Hayato Mizoguchi, Takahama (JP); Tsuneo Maebara, Nagoya (JP)

(73) Assignee: DENSO CORPORATION, Kariya (JP)

( * ) Notice: Subject to any disclaimer, the term of this patent is extended or adjusted under 35 U.S.C. 154(b) by 195 days.

(21) Appl. No.: 13/933,852

(22) Filed: Jul. 2, 2013

(65) Prior Publication Data
US 2014/0002096 A1   Jan. 2, 2014

(30) Foreign Application Priority Data

Jul. 2, 2012 (JP) .................................. 2012-148594

(51) Int. Cl.
| | |
|---|---|
| G01R 31/00 | (2006.01) |
| G01R 31/02 | (2006.01) |
| A61B 5/021 | (2006.01) |
| G01L 9/00 | (2006.01) |
| G01R 27/18 | (2006.01) |
| G01R 1/36 | (2006.01) |

(52) U.S. Cl.
CPC .............. *G01R 31/025* (2013.01); *A61B 5/021* (2013.01); *G01L 9/0041* (2013.01); *G01R 1/36* (2013.01); *G01R 27/18* (2013.01); *G01R 31/006* (2013.01)

(58) Field of Classification Search
CPC ............................ G01R 31/025; G01L 9/0041
USPC ........................... 324/158, 378, 379, 500, 503
See application file for complete search history.

(56) References Cited

U.S. PATENT DOCUMENTS

| 4,799,769 A | 1/1989 | Demura et al. | |
|---|---|---|---|
| 2008/0167793 A1 | 7/2008 | Kaneko et al. | |
| 2013/0280697 A1* | 10/2013 | Leying et al. ..................... | 435/5 |
| 2013/0314097 A1* | 11/2013 | Hausberger et al. .......... | 324/503 |
| 2014/0153146 A1* | 6/2014 | Tsen et al. ...................... | 361/56 |

FOREIGN PATENT DOCUMENTS

| JP | 3-45871 | 9/1991 |
|---|---|---|
| JP | 4-79180 | 12/1992 |

(Continued)

OTHER PUBLICATIONS

Japanese Office Action (3 pgs.) dated Jun. 3, 2014 issued in corresponding Japanese Application No. 2012-148594 with an at least partial English-language translation thereof (4 pgs.).

*Primary Examiner* — Jermele M Hollington
*Assistant Examiner* — Raul Rios Russo
(74) *Attorney, Agent, or Firm* — Nixon & Vanderhye PC

(57) ABSTRACT

An apparatus capable of detecting reduction in insulation resistance between a vehicle body and a high-voltage circuit. In the apparatus, a filter for removing noise included in a potential to ground at a terminal of a coupling capacitor includes a digital filter and an aliasing suppression circuit for suppressing aliasing in the digital filter. In addition, a protection circuit, which protects the digital filter and a determiner operable to detect the reduction in insulation resistance from high-voltage noise generated in the high-voltage circuit, is electrically disposed between a resistor of the aliasing suppression circuit and a signal input of the digital filter, where a potential at a junction between the resistor of the aliasing suppression circuit and the signal input of the digital filter is lower than a potential at the terminal of the coupling capacitor upon application of the high-voltage noise to the apparatus.

10 Claims, 5 Drawing Sheets

(56) References Cited

FOREIGN PATENT DOCUMENTS

| JP | 2003-274504 | 9/2003 |
| JP | 3781289 | 3/2006 |
| JP | 2007-114173 | 5/2007 |
| JP | 2008-169728 | 7/2008 |
| JP | 2010-8356 | 1/2010 |

* cited by examiner

INSULATION DETERIORATION DETECTION APPARATUS

CROSS-REFERENCE TO RELATED APPLICATION

This application is based on and claims the benefit of priority from earlier Japanese Patent Application No. 2012-148594 filed Jul. 2, 2012, the description of which is incorporated herein by reference.

BACKGROUND

1. Technical Field

The present invention relates to an apparatus configured to detect reduction in insulation resistance between a vehicle body and a high-voltage circuit.

2. Related Art

A formerly known vehicle including a high-voltage battery system including a high-voltage circuit, such as a hybrid vehicle or an electrical vehicle, is equipped with an apparatus which detects reduction in insulation resistance between a vehicle body and the high-voltage circuit, for ensuring safety of occupants or the like (see, for example, Japanese Patent No. 3781289).

The apparatus disclosed in Japanese Patent No. 3781289 adopts a technique for detecting insulation deterioration between the vehicle body and the high-voltage circuit on the basis of a change in magnitude of a potential to ground at a first terminal of a coupling capacitor, which is in turn electrically connected to the high-voltage circuit at a predefined point of the high-voltage circuit via a second terminal of the coupling capacitor, during application of an AC voltage of predetermined frequency to the first terminal of the coupling capacitor through a predetermined output impedance.

To remove high-voltage noise generated in the high-voltage circuit, the apparatus disclosed in Japanese Patent No. 3781289 includes an analog filter, such a bandpass filter or a highpass filter, electrically connected between the first terminal of the coupling capacitor and a determiner that determines reduction in insulation resistance between the vehicle body and the high-voltage circuit.

In the apparatus disclosed in Japanese Patent No. 3781289, the analog filter is used for removing high-voltage noise generated in the high-voltage circuit. However, since various properties of the analog filter may alter due to, for example, a temperature variation and aging degradation and the like of each of elements constituting the analog filter, the accuracy of detecting insulation resistance between the vehicle body and the high-voltage circuit is inevitably low. To improve the detection accuracy, a temperature-compensated element may be included additionally in the analog filter. This however may lead to a more complicated configuration of the filter circuit and thus to increased cost.

In addition, since the high-voltage noise generated in the high-voltage circuit may be applied to the determiner, as a microcomputer or the like, configured to determine the reduction in insulation resistance, via the first terminal of the coupling capacitor that is a measurement point of the potential to ground, a protection circuit formed of high voltage-resistance elements may be provided to protect the determiner. This may lead to further increased cost.

In consideration of the foregoing, it would therefore be desirable to have an apparatus capable of improving accuracy of detecting reduction in insulation resistance between a vehicle body and a high-voltage circuit while ensuring high voltage resistance with a simpler configuration.

SUMMARY

In accordance with an exemplary embodiment of the present invention, there is provided an apparatus for detecting reduction in insulation resistance between a vehicle body and a high-voltage circuit. In the apparatus, a coupling capacitor is electrically connected to the high-voltage circuit at a predefined point of the high-voltage circuit via a first terminal of the coupling capacitor. An oscillation circuit is configured to apply an AC voltage of a predetermined frequency to a second terminal of the coupling capacitor through a predetermined output impedance. A determiner is configured to determine reduction in insulation resistance between the vehicle body and the high-voltage circuit on the basis of a change in potential to ground at the second terminal of the coupling capacitor. A digital filter is configured to remove noise included in the potential to ground to be forwarded to the determiner, where the digital filter is electrically connected between the second terminal of the coupling capacitor and a signal input of the determiner. An aliasing suppression circuit is configured to suppress aliasing in the digital filter, where the aliasing suppression circuit is electrically connected between the second terminal of the coupling capacitor and a signal input of the digital filter, and the aliasing suppression circuit includes a resistor electrically connected to the second terminal of the coupling capacitor. A protection circuit is configured to protect the determiner and the digital filter from high-voltage noise generated in the high-voltage circuit, where the protection circuit is electrically disposed between the resistor of the aliasing suppression circuit and the signal input of the digital filter.

With this configuration, the filter for removing noise included in the potential to ground at the second terminal of the coupling capacitor includes the digital filter having a higher signal to noise ratio than an analog filter, and the aliasing suppression circuit for suppressing aliasing in the digital filter. This allows the determiner to more accurately detect the potential to ground at the second terminal of the coupling capacitor.

In addition, the protection circuit is electrically disposed between the resistor of the aliasing suppression circuit and the signal input of the digital filter, where a potential at a junction between the resistor of the aliasing suppression circuit and the signal input of the digital filter is lower than a potential at the second terminal of the coupling capacitor upon application of the high-voltage noise to the apparatus. This can ensure high voltage resistance without using high voltage-resistance elements or the like for the protection circuit.

This leads to a higher accuracy of detecting reduction in insulation resistance between the high-voltage circuit and the vehicle body while ensuring high voltage resistance of the apparatus with a simpler configuration.

DESCRIPTION OF SPECIFIC EMBODIMENTS

Figure 1:
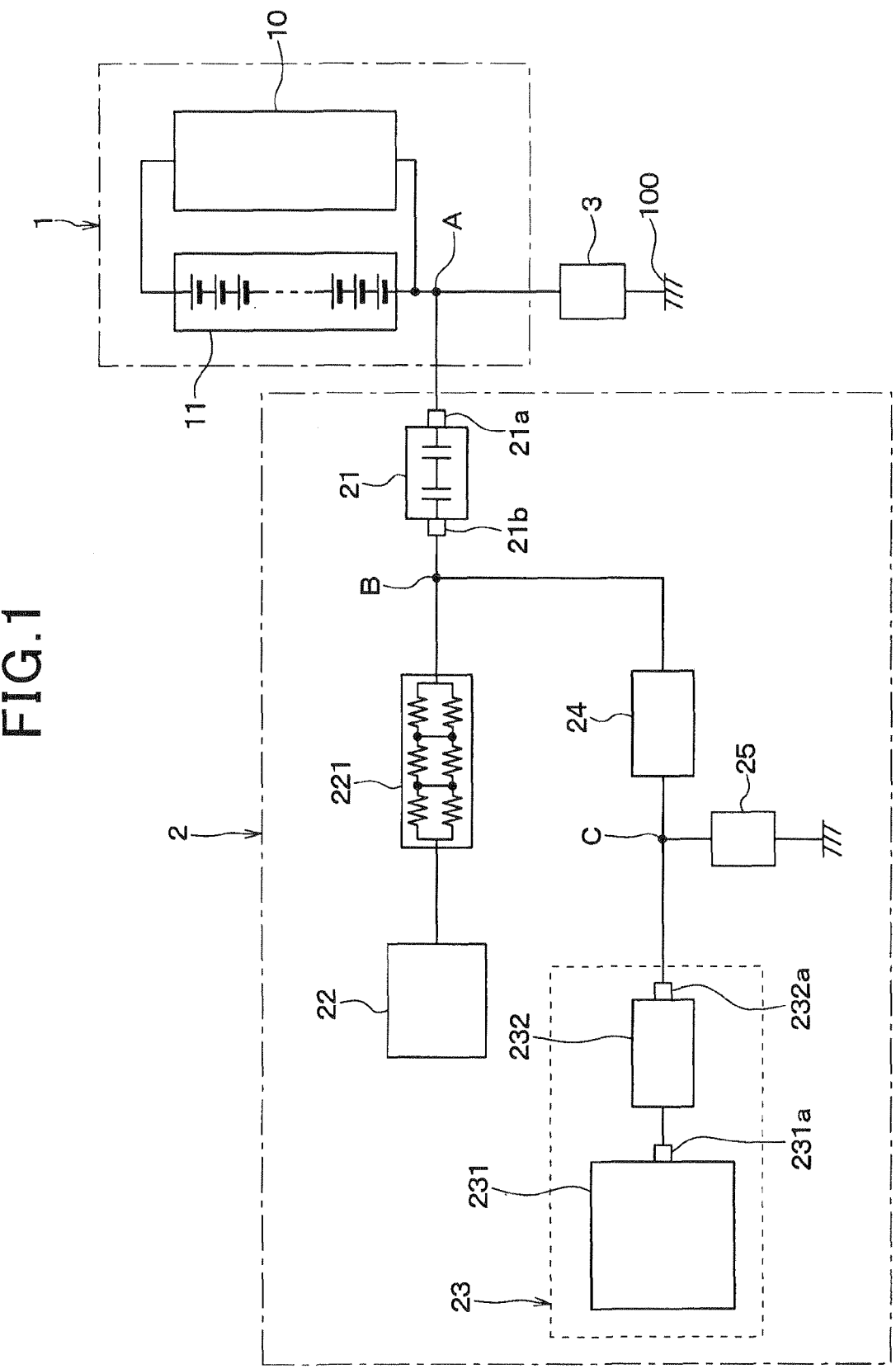
FIG. 1 shows a schematic block diagram of an insulation deterioration detection apparatus in accordance with a first embodiment of the present invention.

The present invention will be described more fully hereinafter with reference to the accompanying drawings in which specific embodiments of the invention are shown. Like numbers refer to like elements throughout.

(First Embodiment)

There will now be explained a first embodiment of the present invention. An insulation deterioration detection apparatus 2 of the present embodiment is configured to detect reduction in insulation resistance between a vehicle body 100 and a high-voltage circuit 1 mounted in the vehicle, and is applicable to a vehicle equipped with a high-voltage battery 11, such as a hybrid vehicle or an electrical vehicle.

The high-voltage circuit 1 includes various electrical loads 10, such as a vehicle prime mover and the like, and a high-voltage battery 11 that supplies electrical power to the electrical loads 10. The high-voltage battery 11 is a high-voltage power supply (e.g., of 300V) including an assembled battery, such as a series connection of a plurality of lithium-ion batteries or the like.

Basically, the high-voltage battery 11 of the high-voltage circuit 1 is electrically isolated from the vehicle body 100. However, there actually exists, for example, a ground insulation resistor 3 of several MΩ or more between the vehicle body 100 and each element of the high-voltage battery 11. For illustration, in FIG. 1, the ground insulation resistor 3 is electrically connected to a negative terminal of the high-voltage battery 11.

The insulation deterioration detection apparatus 2, which detects deterioration of the ground insulation resistor 3 between the high-voltage circuit 1 and the vehicle body 100, is electrically connected to the negative terminal of the high-voltage battery 11 of the high-voltage circuit 1.

The insulation deterioration detection apparatus 2 includes a coupling capacitor 21, an oscillation circuit 22, a control circuit 23, an aliasing suppression circuit 24, and a protection circuit 25.

The coupling capacitor 21, which electrically isolates the insulation deterioration detection apparatus 2 from the high-voltage circuit 1, has a first terminal 21a electrically connected to the negative terminal of the high-voltage battery 11 of the high-voltage circuit 1.

The oscillation circuit 22, which outputs an AC voltage (e.g., of 5V) of a predetermined frequency (e.g., of 2.5Hz), is electrically connected to a second terminal 21b of the coupling capacitor 21 through an output impedance 221 having a predetermined resistance value (e.g., 100-150Ω). That is, the oscillation circuit 22 applies the AC voltage of the predetermined frequency to the second terminal 21b of the coupling capacitor 21 through the output impedance 221.

The control circuit 23 includes a microcomputer composed of CPU, ROM, RAM, EEPROM and the like, and its peripherals. The control circuit 23 performs various processes according to control programs stored in storage means, such as ROM.

In the present embodiment, the control circuit 23 includes a determiner 231 that determines a reduced insulation resistance between the high-voltage circuit 1 and the vehicle body 100, and a digital filter 232 that removes noise included in a potential to ground to be forwarded to the determiner 231.

The determiner 231 is configured to determine a reduced insulation resistance between the high-voltage circuit 1 and the vehicle body 100 on the basis of a change in magnitude of the potential to ground at the second terminal of the coupling capacitor 21. For example, the determiner 231 determines that a resistance value of the ground insulation resistor 3 is reduced when the magnitude of the potential forwarded to the determiner 231 becomes greater than that of a reference potential.

The digital filter 232, which converts a received analog signal to a digital signal and removes noise included in the digital signal, is electrically connected between the second terminal 21b of the coupling capacitor 21 and a signal input 231a of the determiner 231. In the present embodiment, the digital filter 232 is configured to extract from the received signal a frequency component corresponding to a predetermined frequency and feeds the extracted component to the determiner 231. A finite impulse response (FIR) filter may be used as the digital filter 232.

Figure 2:
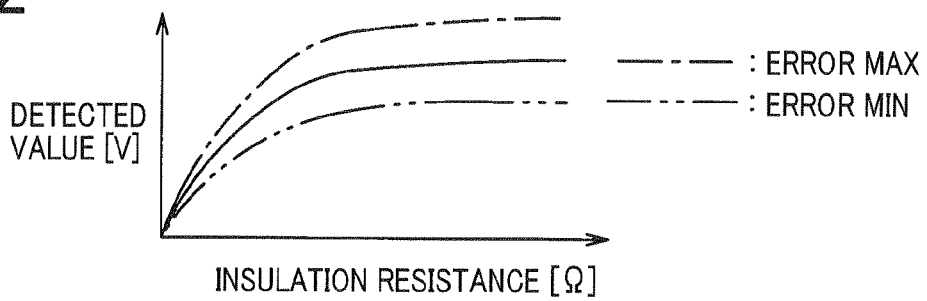
FIG. 2 shows curves for explaining accuracy of detection of a potential to ground carried out in a determiner using an analog filter.

With the analog filter being used as the filter for removing noise included in the signal to be forwarded to the determiner 231, for example, as shown in FIG. 2, detection errors of the potential to ground detected by the determiner 231 may be much increased with increasing insulation resistance due to a temperature variation and/or aging degradation or the like.

Figure 3:
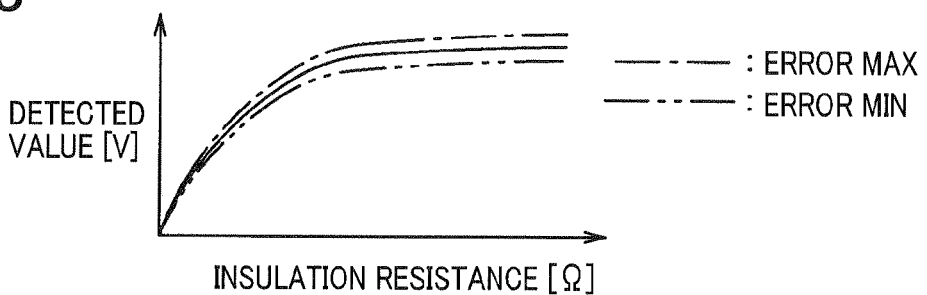
FIG. 3 shows curves for explaining accuracy of detection of a potential to ground carried out in a determiner using a digital filter.

In contrast, in the present embodiment, the digital filter 232, less affected with a temperature variation and/or aging degradation or the like, is used as the filter for removing noise included in the signal to be forwarded to the determiner 231. Accordingly, for example, as shown in FIG. 3, detection errors of the potential to ground detected by the determiner 231 may be less increased even with increasing insulation resistance. As such, use of the digital filter 232 that is capable of providing a higher signal to noise ratio than the analog filter can lead to a higher detection accuracy of the potential to ground at the second terminal 21b of the coupling capacitor 21 to be detected by the determiner 231.

The aliasing suppression circuit 24, which prevents aliasing from occurring during conversion of the analog signal to the digital signal in the digital filter 232, is electrically connected between the second terminal 21b of the coupling capacitor 21 and a signal input 232a of the digital filter 232.

In the present embodiment, the aliasing suppression circuit 24 serves as a low-pass filter adapted to remove, from the analog signal, frequency components of frequencies equal to or higher than a predetermined reference frequency as aliasing noise and feeds the noise free signal to the digital filter 232. The reference frequency is set equal to or higher than half a sampling frequency of the digital filter 232.

Figure 4:
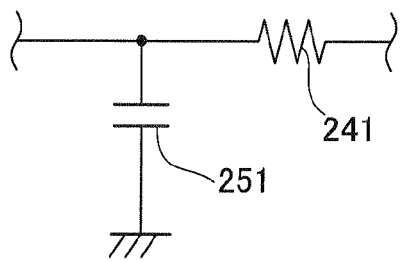
FIG. 4 shows a circuit diagram of an aliasing suppression circuit and a protection circuit in accordance with the first embodiment.

More specifically, in the present embodiment, as shown in FIG. 4, the aliasing suppression circuit 24 serves as a passive filter formed of passive elements including a resistor 241 electrically connected to the second terminal 21b of the coupling capacitor 21 and a grounding capacitor 251 forming a protection circuit 25 (which will be explained later). The aliasing suppression circuit 24 of the present embodiment shares the grounding capacitor 251 with the protection circuit 25.

The protection circuit 25 protects the determiner 231 and the digital filter 232 of the control circuit 23 from the high-voltage noise generated in the high-voltage circuit 1. The protection circuit 25 is electrically disposed between the second terminal 21b of the coupling capacitor 21 and the signal input 232a of the digital filter 232, more particularly, between the resistor 241 of the aliasing suppression circuit 24 and the signal input 232a of the digital filter 232.

In the present embodiment, the protection circuit 25 includes the grounding capacitor 251 such that a first terminal of the grounding capacitor 251 is electrically connected to a junction between the resistor 241 of the aliasing suppression circuit 24 and the signal input 232a of the digital filter 232 and a second terminal of the grounding capacitor 251 is grounded to the vehicle body 100.

There will now be explained the operations of the insulation deterioration detection apparatus 2 in accordance with the present embodiment.

In the absence of insulation deterioration between the high-voltage circuit 1 and the vehicle body 100, the ground insulation resistor 3 is of high resistance, which leads to a low voltage drop across the output impedance 221 and thus to a low potential to ground at the second terminal 21b of the coupling capacitor 21. Accordingly, since the potential to ground detected by the determiner 231 of the control circuit 23 is of low magnitude, the determiner 231 will determine that insulation deterioration of the ground insulation resistor 3 has not occurred.

In the presence of insulation deterioration between the high-voltage circuit 1 and the vehicle body 100, the ground insulation resistor 3 is of low resistance, which leads to an increased voltage drop of the AC voltage across the output impedance 221. Accordingly, since the potential to ground detected by the determiner 231 of the control circuit 23 is of high magnitude, the determiner 231 will determine that insulation deterioration of the ground insulation resistor 3 has occurred.

There will now be explained changes in potential within the insulation deterioration detection apparatus 2 when the high-voltage noise generated in the high-voltage circuit is applied to the insulation deterioration detection apparatus 2.

Figure 5:
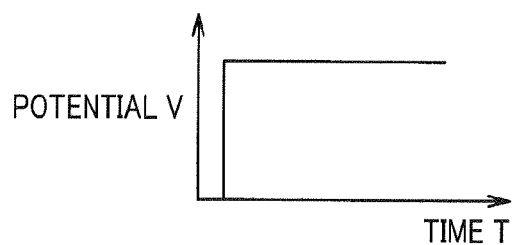
FIG. 5 shows a change in potential within the insulation deterioration detection apparatus upon application of high-voltage noise from a high-voltage circuit to the insulation deterioration detection apparatus.
Figure 6:
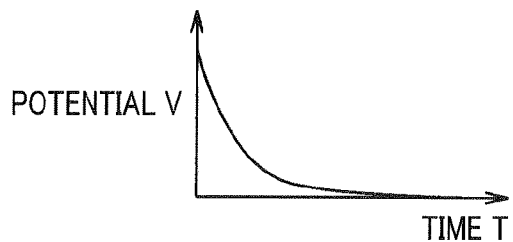
FIG. 6 shows a change in potential within the insulation deterioration detection apparatus upon application of high-voltage noise from the high-voltage circuit to the insulation deterioration detection apparatus.

For example, when a square wave (e.g., of hundreds of volts) as shown in FIG. 5, as the high-voltage noise, is applied at the point A shown in FIG. 1 between the high-voltage circuit 1 and the first terminal 21a of the coupling capacitor 21, a potential at the point B shown in FIG. 1 changes as shown in FIG. 6. Meanwhile, when a square wave as shown in FIG. 5, as the high-voltage noise, is applied at the point B shown in FIG. 1, a potential at the point C shown in FIG. 1 changes as shown in FIG. 7.

Figure 7:
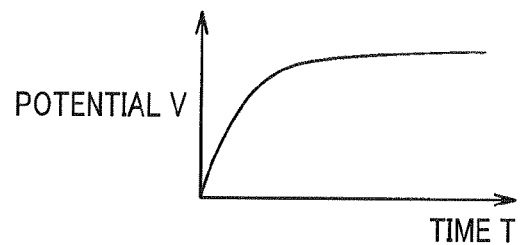
FIG. 7 shows a change in potential within the insulation deterioration detection apparatus upon application of high-voltage noise from the high-voltage circuit to the insulation deterioration detection apparatus.
Figure 8:
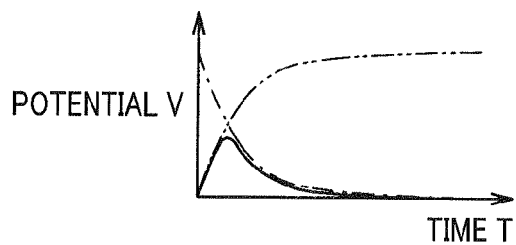
FIG. 8 shows a change in potential within the insulation deterioration detection apparatus upon application of high-voltage noise from the high-voltage circuit to the insulation deterioration detection apparatus.

When the square wave as shown in FIG. 5 is applied at the point A shown in FIG. 1 as the high-voltage noise, the potential at the point C shown in FIG. 1 changes as shown in FIG. 8 (see the solid line) without exceeding both the curve indicating the potential change shown in FIG. 6 (long dashed short dashed line shown in FIG. 8) and the curve indicating the potential change shown in FIG. 7 (long dashed double-short dashed line shown in FIG. 8).

Even when the high-voltage noise is applied from the high-voltage circuit 1 to the insulation deterioration detection apparatus 2, the potential at the point C shown in FIG. 1 connected to the protection circuit 25 is of much lower magnitude than the potential at the point B shown in FIG. 1. Accordingly, even though the protection circuit 25 is comprised of low voltage-resistance elements, the determiner 231 and the digital filter 232 of the control circuit 23 can be protected.

As described above, in the insulation deterioration detection apparatus 2 of the present embodiment, the filter for removing noise included in the potential to ground at the second terminal 21b of the coupling capacitor 21 includes the digital filter 232 having a higher signal to noise ratio than the analog filter, and the aliasing suppression circuit 24 for suppressing aliasing in the digital filter 232. This allows the determiner 231 to more accurately detect the potential to ground at the second terminal 21b of the coupling capacitor 21.

In addition, in the present embodiment, the protection circuit 25 is connected to the point C between the resistor 241 of the aliasing suppression circuit 24 and the signal input 232a of the digital filter 232, where the potential at the point C is lower than the potential at the second terminal 21b of the coupling capacitor 21 upon application of the high-voltage noise. This can ensure high voltage resistance without using high voltage-resistance elements or the like for the protection circuit 25.

This leads to a higher accuracy of detecting reduction in insulation resistance between the high-voltage circuit 1 and the vehicle body 100 while ensuring high voltage resistance of the insulation deterioration detection apparatus 2 with a simpler configuration.

Further, in the present embodiment, the aliasing suppression circuit 24 shares the grounding capacitor 251 with the protection circuit 25. This leads to a simpler configuration of the insulation deterioration detection apparatus 2.

(Second Embodiment)

There will now be explained a second embodiment of the present invention. Elements of the present embodiment similar or equivalent to those described in the first embodiment will not be explained or will be explained in a simplified manner.

Figure 9:
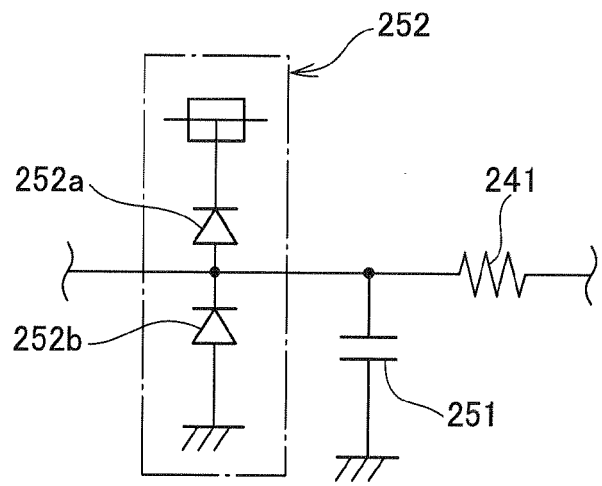
FIG. 9 shows a circuit diagram of an aliasing suppression circuit and a protection circuit in accordance with a second embodiment of the present invention.

In the present embodiment, as shown in a circuit diagram of FIG. 9, the protection circuit 25 includes a grounding capacitor 251 and a voltage limiter circuit 252 formed of clamping diodes 252a, 252b.

The voltage limiter circuit 252 is electrically disposed between the grounding capacitor 251 and the signal input 232a of the digital filter 232, and limits a voltage to be inputted to the digital filter 232.

In the present embodiment, the protection circuit 25 additionally includes the voltage limiter circuit 252. This leads to more secure protection of the determiner 231 and the digital filter 232 of the control circuit 23 from the high-voltage noise generated in the high-voltage circuit 1.

Figure 10:
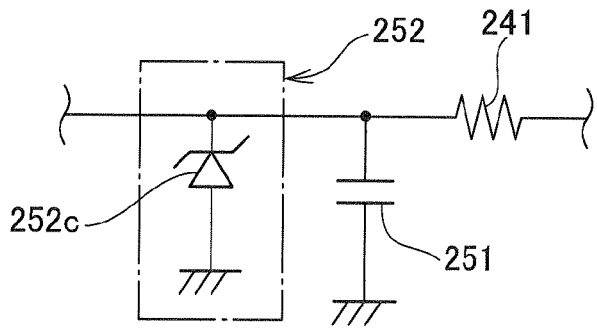
FIG. 10 shows a variation of the embodiment shown in FIG. 9.

Alternatively, the voltage limiter circuit 252 may be formed not of the clamping diodes 252a, 252b, but of a zener diode 252c as shown in the circuit diagram of FIG. 10. Still alternatively, the voltage limiter circuit 252 may be formed of the clamping diode 252a, 252b and the zener diode 252c.

(Third Embodiment)

There will now be explained a third embodiment of the present invention. Elements of the present embodiment similar or equivalent to those described in any one of the first and second embodiments will not be explained or will be explained in a simplified manner.

Figure 11:
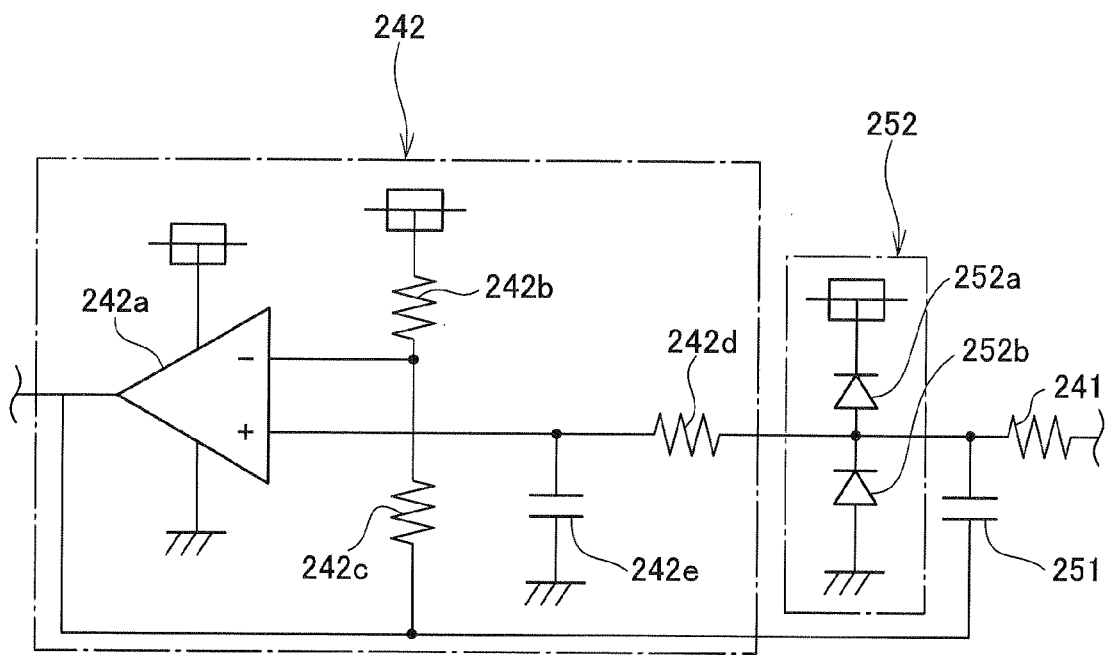
FIG. 11 shows a circuit diagram of an aliasing suppression circuit and a protection circuit in accordance with a third embodiment of the present invention.

The present embodiment is similar to each of the first and second embodiments except that, as shown in FIG. 11, the aliasing suppression circuit 24 includes, in addition to the resistor 241 and the grounding capacitor 251, an amplifier circuit 242 as an active filter. The amplifier circuit 242 includes an operational amplifier 242a as an active element, resistors 242b-242d and a capacitor 242e as passive elements. In the present embodiment, the protection circuit 25 is electrically disposed between the resistor 241 of the aliasing suppression circuit 24 electrically connected to the second terminal 21b of the coupling capacitor 21, and the amplifier circuit 242.

Figure 12:
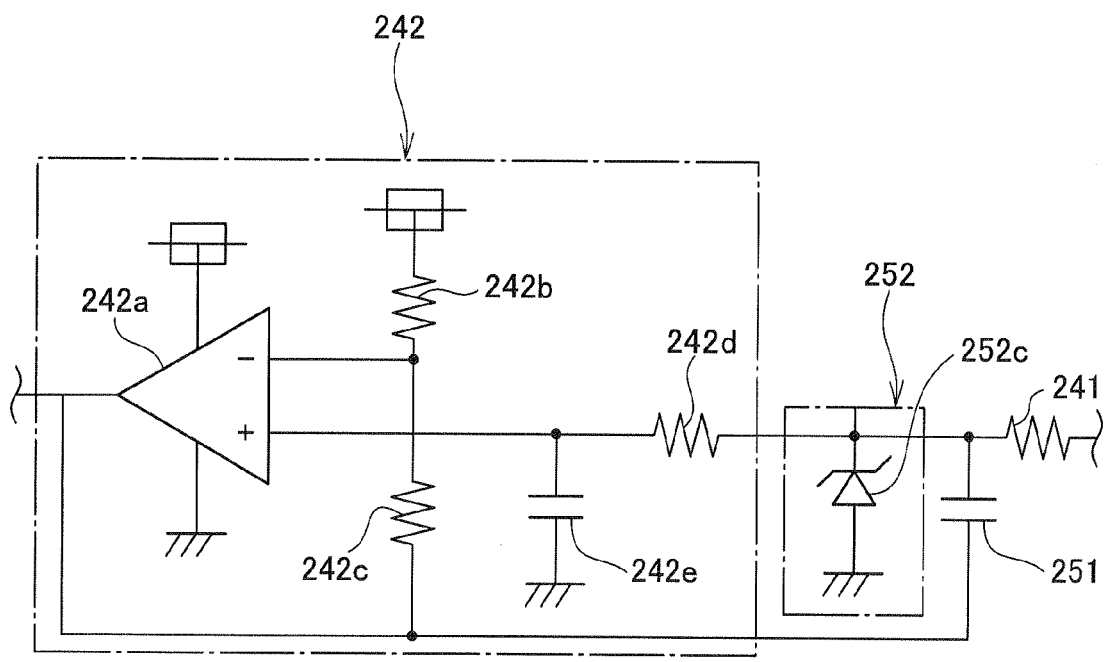
FIG. 12 shows a variation of the embodiment shown in FIG. 11.

The present embodiment provides similar benefits as in the first and second embodiments. In the present embodiment, as shown in FIG. 11, the voltage limiter circuit 252 is formed of clamping diodes 252a, 252b. Alternatively, as shown in the circuit diagram of FIG. 12, the voltage limiter circuit 252 may be formed of a zener diode 252c.

(Fourth Embodiment)

There will now be explained a fourth embodiment of the present invention. Elements of the present embodiment similar or equivalent to those described in any one of the first to third embodiments will not be explained or will be explained in a simplified manner.

Figure 13:
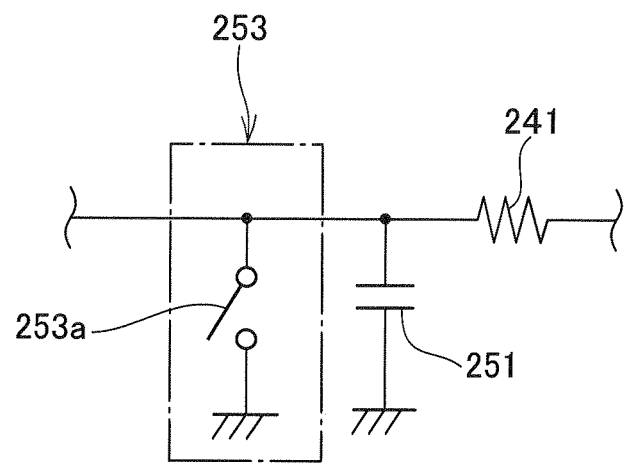
FIG. 13 shows a circuit diagram of an aliasing suppression circuit and a protection circuit in accordance with a fourth embodiment of the present invention.

In the present embodiment, as shown in the circuit diagram of FIG. 13, the protection circuit 25 includes a grounding capacitor 251, and an over-current protector (as over-current protection means) 253 formed of a switching element 253a.

The over-current protector 253 is electrically disposed between the grounding capacitor 251 and the signal input 232a of the digital filter 232. The over-current protector 253 is operable to, when the high-voltage noise generated in the high-voltage circuit 1 is applied to the insulation deterioration detection apparatus 2, turn on the switching element 253a so as to make the junction between the grounding capacitor 251 and the digital filter 232 shorted to earth.

Addition of the over-current protector 253 to the protection circuit 25 can prevent an overcurrent caused by the high-voltage noise from flowing through the determiner 231 and the digital filter 232. This leads to more secure protection of the determiner 231 and the digital filter 232 of the control circuit 23 from the high-voltage noise generated in the high-voltage circuit 1.

Figure 14:
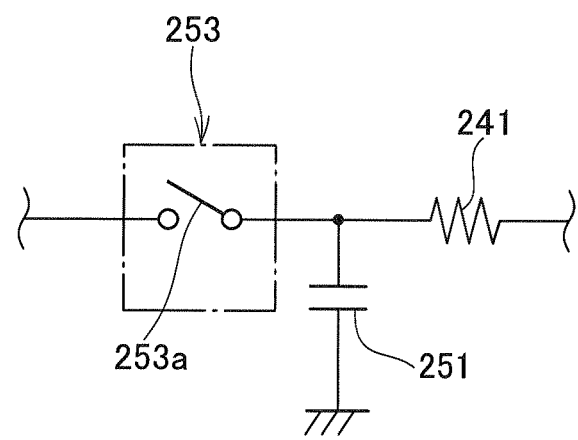
FIG. 14 shows a variation of the embodiment shown in FIG. 13.

In the present embodiment shown in FIG. 13, the over-current protector 253 is operable to, when the high-voltage noise generated in the high-voltage circuit 1 is applied to the insulation deterioration detection apparatus 2, turn on the switching element 253a so as to make the junction between the grounding capacitor 251 and the digital filter 232 shorted to earth. Alternatively, for example, as shown in FIG. 14, the over-current protector 253 may be configured to, when the high-voltage noise generated in the high-voltage circuit 1 is applied to the insulation deterioration detection apparatus 2, turn off the switching element 253a so as to interrupt the electrical connection between the grounding capacitor 251 and the digital filter 232.

(Other Embodiments)

While the present invention has been described with respect to a limited number of embodiments, those skilled in the art will appreciate numerous modifications and variations therefrom. There will now be explained some modifications of the above described embodiments that may be devised without departing from the spirit and scope of the present invention.

(1) The use of the aliasing suppression circuit 24 and the protection circuit 25 described in each of the first to fourth embodiments is an example only. Each of these components may be used optionally as appropriate.

(2) In each of the first to fourth embodiments, the aliasing suppression circuit 24 shares the grounding capacitor 251 with the protection circuit 25. Alternatively, the protection circuit 25 and the aliasing suppression circuit 24 may include their respective separate grounding capacitors.

(3) In each of the first to fourth embodiments, the first terminal 21a of the coupling capacitor 21 is electrically connected to the negative terminal of the high-voltage battery 11 in the high-voltage circuit 1. Alternatively, the first terminal 21a of the coupling capacitor 21 may electrically be connected to the high-voltage circuit 1 at any point thereof.

(4) The aforementioned features of each of the first to fourth embodiments may be combined with any of the other embodiments of the present invention as appropriate.

What is claimed is:

1. An apparatus for detecting reduction in insulation resistance between a vehicle body and a high-voltage circuit, the apparatus comprising:
   a coupling capacitor electrically connected to the high-voltage circuit at a predefined point of the high-voltage circuit via a first terminal of the coupling capacitor;
   an oscillation circuit configured to apply an AC voltage of a predetermined frequency to a second terminal of the coupling capacitor through a predetermined output impedance;
   a determiner configured to determine reduction in insulation resistance between the vehicle body and the high-voltage circuit on the basis of a change in potential to ground at the second terminal of the coupling capacitor;
   a digital filter configured to remove noise included in the potential to ground to be forwarded to the determiner, the digital filter being electrically connected between the second terminal of the coupling capacitor and a signal input of the determiner;
   an aliasing suppression circuit configured to suppress aliasing in the digital filter, the aliasing suppression circuit being electrically connected between the second terminal of the coupling capacitor and a signal input of the digital filter, and the aliasing suppression circuit including a resistor electrically connected to the second terminal of the coupling capacitor; and
   a protection circuit configured to protect the determiner and the digital filter from high-voltage noise generated in the high-voltage circuit, the protection circuit being electrically disposed between the resistor of the aliasing suppression circuit and the signal input of the digital filter.

2. The apparatus of claim 1, wherein the protection circuit comprises a grounding capacitor, a first terminal of the grounding capacitor being electrically connected to a junction between the resistor of the aliasing suppression circuit and the signal input of the digital filter, and a second terminal of the grounding capacitor being electrically connected to the vehicle body.

3. The apparatus of claim 2, wherein the protection circuit further comprises a voltage limiter circuit configured to limit a voltage to be inputted to the digital filter, the voltage limiter circuit being electrically disposed between the grounding capacitor and the signal input of the digital filter.

4. The apparatus of claim 3, wherein the voltage limiter circuit comprises at least one diode.

5. The apparatus of claim 4, wherein the at least one diode includes a pair of clamping diodes.

6. The apparatus of claim 4, wherein the at least one diode includes a zener diode.

7. The apparatus of claim 2, wherein the protection circuit further comprises an over-current protector configured to prevent an overcurrent caused by the high-voltage noise from flowing through the determiner and the digital filter.

8. The apparatus of claim 7, wherein the over-current protector comprises a normally-open switch, a first terminal of the switch being electrically connected to a junction between the first terminal of the grounding capacitor and the signal input of the digital filter, a second terminal of the switch being electrically connected to the vehicle body, and the switch being configured to be turned on or closed upon application of the high-voltage noise generated in the high-voltage circuit to the apparatus.

9. The apparatus of claim 7, wherein the over-current protector comprises a normally-closed switch, the switch being electrically connected between the first terminal of the grounding capacitor and the signal input of the digital filter, and the switch being configured to be turned off or opened upon application of the high-voltage noise generated in the high-voltage circuit to the apparatus.

10. The apparatus of claim 2, wherein the aliasing suppression circuit shares the grounding capacitor with the protection circuit.

* * * * *